United States Patent
Anderson et al.

(10) Patent No.: US 6,818,654 B2
(45) Date of Patent: Nov. 16, 2004

(54) ANTIBACTERIAL COMPOUNDS

(75) Inventors: David Anderson, Kenosha, WI (US); Bruce Beutel, Lake Forest, IL (US); Curt Cooper, Vernon Hills, IL (US); Peter Dandliker, Gurnee, IL (US); Caroline David, Green Oaks, IL (US); Yu-Gui Gu, Libertyville, IL (US); Mira Hinman, Libertyville, IL (US); Douglas Kalvin, Buffalo Grove, IL (US); Linda Lynch, Pleasant Prairie, WI (US); Zhenkun Ma, Dallas, TX (US); Christopher Motter, Sturtevant, WI (US); Teresa Rosenberg, Gurnee, IL (US); William Sanders, Fox Lake, IL (US); Michael Tufano, Chicago, IL (US); Rolf Wagner, Gurnee, IL (US); Moshe Weitzberg, Highland Park, IL (US); Hong Yong, Grayslake, IL (US)

(73) Assignee: Abbott Laboratories, Abbott Park, IL (US)

(*) Notice: Subject to any disclaimer, the term of this patent is extended or adjusted under 35 U.S.C. 154(b) by 28 days.

(21) Appl. No.: 10/386,816

(22) Filed: Mar. 12, 2003

(65) Prior Publication Data

US 2004/0072817 A1 Apr. 15, 2004

Related U.S. Application Data

(60) Provisional application No. 60/363,480, filed on Mar. 12, 2002.

(51) Int. Cl.$^7$ .............................. C07D 215/00; A61K 31/47
(52) U.S. Cl. ........................................ 514/312; 546/156
(58) Field of Search .............................. 514/312; 546/156

(56) References Cited

U.S. PATENT DOCUMENTS

| | | | | | |
|---|---|---|---|---|---|
| 4,774,246 A | * | 9/1988 | Chu | ........................ | 514/253.08 |
| 5,385,900 A | * | 1/1995 | Konno et al. | ................. | 514/218 |

* cited by examiner

Primary Examiner—Zinna Northington Davis
(74) Attorney, Agent, or Firm—B. Coregory Donner

(57) ABSTRACT

Antibacterials having formula (I)

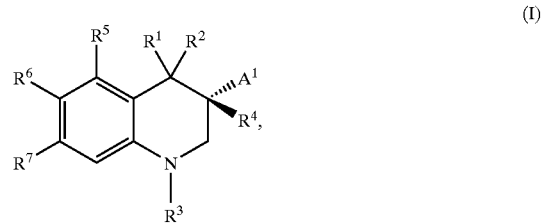

and salts, prodrugs, and salts of prodrugs thereof, processes for making the compounds and intermediates used in the processes, compositions containing the compounds, and methods of prophylaxis and treatment of bacterial infections using the compounds are disclosed.

6 Claims, No Drawings

ANTIBACTERIAL COMPOUNDS

This application claims the benefit of U.S. Provisional Application Ser No. 60/363,480, filed Mar. 12, 2002, the specification of which is hereby incorporated by reference into this application.

TECHNICAL FIELD

This invention is directed to compounds having antibacterial activity, processes for making the compounds and intermediates used in the processes, compositions containing the compounds, and methods for prophylaxis and treatment of bacterial infections using the compounds.

BACKGROUND OF THE INVENTION

Because the effectiveness of many drugs currently available for prophylaxis and treatment of bacterial infections is being compromised by the emergence of drug-resistant bacteria, the introduction of novel antibacterials would be beneficial for their therapeutic value and their contribution to the antibacterial arts.

SUMMARY OF THE INVENTION

Accordingly, the first embodiment of this invention is directed to compounds, and salts, prodrugs, and salts of prodrugs thereof, which are useful as antibacterials, the compounds having formula (I)

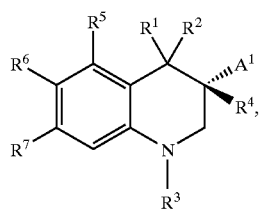

(I)

in which
one of $A^1$ or $R^4$ is OH or $OR^{11}$ and the other is C(O)OH or $C(O)OR^{60}$;
$R^1$ and $R^2$ are hydrogen or taken together are =O;
$R^3$ is hydrogen, $C(CH_3)_3$, $O-CH_2CH=CH_2$, or methyl substituted with 2,4-dimethoxyphenyl;
$R^5$ is hydrogen, alkyl, halo, OH, $CF_3$, $CH_2CF_3$, $CF_2CF_3$, or $OR^{11}$;
$R^6$ is hydrogen, halogen, alkyl, CN, $NO_2$, C(O)H, C≡CH, C≡C(alkyl), C≡CCl$_3$, C≡CCF$_3$, CH=CH$_2$, or $OR^{11}$;
$R^7$ is halo, aryl, heteroaryl, heterocyclyl, bicyclic heterocyclyl, $NH(R^{12})$, or $N(R^{13})(R^{14})$;
$R^{11}$ is alkyl, $C(O)R^{70}$, or alkyl substituted with a substituent selected from the group consisting of halo, aryl, $-NH_2$, $-NH(alkyl)$, and $-N(alkyl)_2$;
$R^{12}$, $R^{13}$, and $R^{14}$ are independently alkyl or alkyl substituted with a substituent selected from the group consisting of heterocyclyl, $-NH_2$, $-NH(alkyl)$, and $-N(alkyl)_2$; and
$R^{60}$ and $R^{70}$ are independently alkyl, aryl, or alkyl substituted with a substituent selected from the group consisting of halo, aryl, $-NH_2$, $-NH(alkyl)$, and $-N(alkyl)_2$;
in which, for the foregoing,
each aryl, heteroaryl, heterocyclyl, and bicyclic heterocyclyl is unsubstituted or substituted with one, two, or three substituents independently selected from the group consisting of alkyl, halo, $-CN$, $-OH$, =O, $-CF_3$, $-OR^{30}$, $-C(O)R^{35}$, $-C(O)OH$, $-C(O)OR^{35}$, $-NH_2$, $-NH(R^{35})$, $-N(R^{35})(R^{36})$, $-C(O)NH_2$, $-C(O)NH(R^{35})$, and $-C(O)N(R^{35})(R^{36})$;

in which
$R^{30}$ is alkyl or alkyl substituted with a substituent selected from the group consisting of halo and $-OR^{45}$;
$R^{35}$ and $R^{36}$ are independently alkyl or alkyl substituted with phenyl; and
$R^{45}$ is alkyl.

A second embodiment is directed to a process for making the compounds of the invention.

A third embodiment is directed to intermediates which are useful in the second embodiment.

A fourth embodiment is directed to compositions for the prophylaxis and treatment of bacterial infections in a fish or a mammal comprising the compounds of the invention and an excipient.

In a preferred fourth embodiment, the bacterial infection is quinoline-resistant bacterial infection.

A fifth embodiment is directed to a method for prophylaxis and treatment of bacterial infection in a fish or a mammal comprising administering thereto a therapeutically effective amount of a compound of the first embodiment.

In a more preferred fifth embodiment, the bacterial infection is quinolone-resistant bacterial infection.

A sixth embodiment of this invention is directed to a method for inhibiting bacterial protein synthesis in a fish or a mammal comprising administering thereto a therapeutically effective amount of a compound, or salt, prodrug, or salt of prodrug thereof, having formula (I)

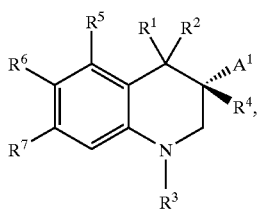

(I)

in which
one of $A^1$ or $R^4$ is OH or $OR^{11}$ and the other is C(O)OH or $C(O)OR^{60}$;
$R^1$ and $R^2$ are hydrogen or taken together are =O;
$R^3$ is hydrogen, $C(CH_3)_3$, $O-CH_2CH=CH_2$, or methyl substituted with 2,4-dimethoxyphenyl;
$R^5$ is hydrogen, alkyl, halo, OH, $CF_3$, $CH_2CF_3$, $CF_2CF_3$, or $OR^{11}$;
$R^6$ is hydrogen, halogen, alkyl, CN, $NO_2$, C(O)H, C≡CH, C≡C(alkyl), C≡CCl$_3$, C≡CCF$_3$, CH=CH$_2$, or $OR^{11}$;
$R^7$ is halo, aryl, heteroaryl, heterocyclyl, bicyclic heterocyclyl, $NH(R^{12})$, or $N(R^{13})(R^{14})$;
$R^{11}$ is alkyl, $C(O)R^{70}$, or alkyl substituted with a substituent selected from the group consisting of halo, aryl, $-NH_2$, $-NH(alkyl)$, and $-N(alkyl)_2$;
$R^{12}$, $R^{13}$, and $R^{14}$ are independently alkyl or alkyl substituted with a substituent selected from the group consisting of heterocyclyl, $-NH_2$, $-NH(alkyl)$, and $-N(alkyl)_2$; and
$R^{60}$ and $R^{70}$ are independently alkyl, aryl, or alkyl substituted with a substituent selected from the group consisting of halo, aryl, $-NH_2$, $-NH(alkyl)$, and $-N(alkyl)_2$;
in which, for the foregoing,
each aryl, heteroaryl, heterocyclyl, and bicyclic heterocyclyl is unsubstituted or subatotuted with one, two, or three substituents independently selected from the group consisting of alkyl, halo, $-CN$, $-OH$, =O, $-CF_3$, $-OR^{30}$, $-C(O)R^{35}$, $-C(O)OH$, $-C(O)OR^{35}$, $-NH_2$, $-NH(R^{35})$, $-N(R^{35})(R^{36})$, $-C(O)NH_2$, $-C(O)NH(R^{35})$, and $-C(O)N(R^{35})(R^{36})$, in which $R^{30}$ is alkyl or alkyl substituted with a substituent selected from the group consisting of halo and —$OR^{45}$;

$R^{35}$ and $R^{36}$ are independently alkyl or alkyl substituted with phenyl; and $R^{45}$ is alkyl.

DETAILED DESCRIPTION OF THE INVENTION

The compounds of the invention comprise a parent moiety and variable moieties, the latter of which are identified by a capital letter and accompanying numerical superscript, and for which the following terms have the meanings indicated.

The term "alkyl" means a monovalent, saturated, straight or branched hydrocarbon, having one to eight carbon atoms, attached through a carbon atom.

The term "alkylene" means a divalent, saturated, straight or branched hydrocarbon, having one to eight carbon atoms, attached through carbon atoms.

The term "aryl" means monovalent phenyl, attached through a carbon atom, unfused or fused with cycloalkyl, cycloalkenyl, heteroaryl, another phenyl, naphthyl, or the saturated part of indan.

The term "bicyclic heterocyclyl" means a monovalent, six-membered ring with one or two nitrogen atoms and the remaining atoms are carbons, zero double bonds, and two non-adjacent carbons attached by a covalent bond or $CH_2$, attached through a nitrogen atom;

a monovalent, seven- or eight-membered ring with one, two, or three nitrogen atoms and the remaining atoms are carbons, zero or one double bonds, and two non-adjacent carbons attached by a covalent bond, attached through the nitrogen atom;

a monovalent, seven- or eight-membered ring with one nitrogen atom and an additional nitrogen, oxygen, or sulfur atom and the remaining atoms are carbons, zero double bonds, and two non-adjacent carbons attached by a covalent bond, attached through a nitrogen atom; and a monovalent, nine-membered ring with one nitrogen atom or one nitrogen atom and an additional nitrogen, oxygen, or sulfur atom and the remaining atoms are carbons, zero or one double bonds, and two non-adjacent carbons or a non-adjacent carbon and nitrogen atom attached by a covalent bond, attached through a nitrogen atom.

The term "cycloalkyl" means a monovalent, saturated cyclic hydrocarbon, having three to eight carbon atoms, attached through a carbon atom.

The term "halo" means fluoro (—F), chloro (—Cl), bromo (—Br), or iodo (—I).

The term "heteroalkylene" means an alkylene of three to eight atoms, connected through a carbon atom, in which one, two, or three $CH_2$ moieties have been independently replaced by —O—, —NH—, —N(alkyl)-, —S, —(C=O)—, —(S=O)—, or —$SO_2$—.

The term "heteroaryl" means a monovalent, aromatic, five-membered ring having two double bonds and one oxygen or one sulfur atom, one, two, three, or four nitrogen atoms, or one or two nitrogen atoms and one oxygen or one sulfur atom and the remaining atoms are carbon atoms, attached through a carbon or nitrogen atom, and unfused or fused with phenyl, cycloalkyl, cycloalkenyl, heterocycle, or another heteroaryl; and a monovalent aromatic, six-membered ring having three double bonds and one, two, or three nitrogen atoms and the remaining atoms are carbon atoms, attached through a carbon atom and unfused or fused with phenyl, cycloalkyl, cycloalkenyl, heterocycle, or another heteroaryl.

The term "heterocyclyl" means a monovalent, non-aromatic three- or four-membered ring having one nitrogen, oxygen, or sulfur atom and the remaining atoms are carbon atoms, zero double bonds, attached through a carbon or nitrogen atom and unfused or fused with phenyl or heteroaryl; a monovalent, non-aromatic five-membered ring having one or two nitrogen, oxygen, or sulfur atoms, and the remaining atoms are carbon atoms, and zero or one double bonds, attached through a carbon or nitrogen atom and unfused or fused with phenyl or heteroaryl; and a monovalent, non-aromatic six or seven-membered ring having one, two, or three nitrogen, oxygen, or sulfur atoms and the remaining atoms are carbon atoms, and zero, one, or two double bonds, attached through a carbon or nitrogen atom and unfused or fused with phenyl or heteroaryl.

A preferred $A^1$ or $R^4$ moiety is —OH and the other is —C(O)OH or —C(O)$OR^{60}$.

Preferred $R^1$ and $R^2$ moieties are ones in which $R^1$ and $R^2$ are hydrogen and $R^1$ and $R^2$ together are =O.

Preferred $R^3$ moieties are hydrogen and —C(CH$_3$)$_3$.

A preferred $R^5$ moiety is hydrogen.

A preferred $R^6$ moiety is —F.

A preferred $R^7$ moiety is 3-aminopyrrolidin-1-yl.

These preferred variable moieties combine with the parent moiety to form a preferred first embodiment of the invention, the embodiment comprising compounds, and salts, prodrugs, and salts of prodrugs thereof, having formula (I)

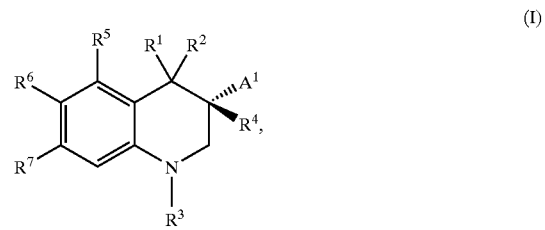

(I)

in which
one of $A^1$ or $R^4$ is OH and the other is —C(O)OH or —C(O)$OR^{60}$;
$R^1$ and $R^2$ are hydrogen or taken together are =O;
$R^3$ is hydrogen or alkyl, in which the alkyl is C(CH$_3$)$_3$;
$R^5$ is hydrogen;
$R^6$ is halo; and
$R^7$ is heterocyclyl,
in which the heterocyclyl is pyrrolidinyl substituted with —NH$_2$.

The preferred variable substituents also combine with the parent moiety to form still yet another preferred first embodiment of this invention, the embodiment comprising compounds, and salts, prodrugs, and salts of prodrugs thereof, which are ethyl 7-(3-aminopyrrolidin-1-yl)-6-fluoro-3-hydroxy-4-oxo-1,2,3,4-tetrahydro-1,8-naphthyridine-3-carboxylate and 7-(3-aminopyrrolidin-1-yl)-6-fluoro-3-hydroxy-4-oxo-1,2,3,4-tetrahydro-1,8-naphthyridine-3-carboxylic acid.

Atoms in the compounds with equimolar amounts of R and S configurations are racemic. Atoms with an excess of one configuration over the other are assigned the configuration in the higher amount, preferably an excess of about 85%–90%, more preferably an excess of about 95%–99%, and still more preferably an excess greater than about 99%.

The terms "R" and "S" are as defined by the IUPAC 1974 Recommendations for Section E, Fundamental Stereochemistry, Pure Appl. Chem. (1976) 45, 13–10.

Accordingly, all stereoisomers of the compounds of the invention, including single enantiomers, racemic mixtures of enantiomers, mixtures of diastereomers, and single diastereomers, are meant to be embraced by the invention.

Geometric isomers, assigned E or Z, may result from the arrangement of substituents around the carbon-carbon or carbon-nitrogen double bond in the compounds. Double bonds with an excess of one arrangement over the other are assigned the arrangement in the higher amount, preferably an excess of about 85%–90%, more preferably an excess of about 95%–99%, and still more preferably an excess of greater than about 99%. The compounds may also exist as an equilibrium mixture comprising two geometric isomers.

Compounds containing hydroxyl, amino, or carboxylic acids may have attached thereto prodrug-forming moieties. The prodrug-forming moieties are removed by metabolic processes and release the compounds having the freed hydroxyl, amino, or carboxylic acid in vivo. Prodrugs are useful for adjusting such pharmacokinetic properties of the compounds as solubility and/or hydrophobicity, absorption in the gastrointestinal tract, bioavailability, tissue penetration, and rate of clearance.

The compounds of the invention may be prepared by synthetic processes or metabolic processes. Metabolic processes include those processes occurring in vitro and in vivo.

The compounds of the invention may exist as acid addition salts, basic addition salts, or zwitterions. Salts of the compounds are prepared during their isolation or following their purification. Acid addition salts of the compounds are those derived from the reaction of the compounds with an acid. For example, the acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, formate, fumarate, hydrochloride, hydrobromide, hydroiodide, lactate, maleate, mesitylenesulfonate, methanesulfonate, naphthylenesulfonate, nicotinate, oxalate, pamoate, pectinate, persulfate, picrate, propionate, succinate, tartrate, thiocyanate, trichloroacetic, trifluoroacetic, phosphate, glutamate, bicarbonate, para-toluenesulfonate, lactobionate, and undecanoate salts of the compounds and prodrugs thereof are contemplated as being within the scope of this invention. When the compounds contain carboxylic acids, basic addition salts may be prepared therefrom by reaction with a base such as the hydroxide, carbonate, or bicarbonate of cations such as lithium, sodium, potassium, calcium, and magnesium.

The compounds of the invention may be administrated with or without another antibacterials and with or without an excipient. Excipients include encapsulating materials or formulation additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, and mixtures thereof. Excipients for orally administered compounds in solid dosage forms include agar, alginic acid, cocoa butter, gelatin, isotonic saline, malt, powdered tragacanth, Ringer's solution, talc, water, aluminum hydroxide, magnesium hydroxide, sodium and potassium phosphate salts, cellulose, cellulose acetate, ethyl cellulose, sodium carboxymethyl cellulose, ethyl laureate, ethyl oleate, magnesium stearate, sodium lauryl sulfate, castor oil, corn oil, cottonseed oil, germ oil, groundnut oil, olive oil, peanut oil, safflower oil, sesame oil, soybean oil, benzyl alcohol, benzyl benzoate, 1,3-butylene glycol, ethanol, ethyl acetate, ethyl carbonate, glycerol, isopropanol, propylene glycol, tetrahydrofurfuryl alcohol, corn starch, potato starch, lactose, glucose sucrose, and mixtures thereof. Excipients for ophthalmically and orally administered compounds in liquid dosage forms include water, ethanol, isopropanol, ethyl carbonate, ethyl acetate, benzyl alcohol, benzyl benzoate, propylene glycol, 1,3-butylene glycol, cottonseed oil, groundnut oil, corn oil, germ oil, olive oil, castor oil, sesame oil, glycerol, tetrahydrofurfuryl alcohol, polyethylene glycols, fatty acid esters of sorbitan, and mixtures thereof. Excipients for osmotically administered compounds include water, ethanol, isopropanol, chlorofluorohydrocarbons, and mixtures thereof. Excipients for parenterally administered compounds include water, 1,3-butanediol, Ringer's solution, U.S.P. or isotonic sodium chloride solution, oleic acid, castor oil, corn oil, cottonseed oil, germ oil, groundnut oil, olive oil, peanut oil, safflower oil, sesame oil, soybean oil, liposomes, and mixtures thereof. Excipients for rectally and vaginally administered compounds include cocoa butter, polyethylene glycol, wax, and mixtures thereof.

The compounds of the invention may be administered parenterally (subcutaneously, intravenously, intramuscularly, and intrasternally), orally, osmotically, ophthalmically, rectally, topically, and vaginally. Orally administered compounds in solid dosage forms may be administered as capsules, dragees, granules, pills, powders, and tablets. Ophthalmically and orally administered compounds in liquid dosage forms may be administered as elixirs, emulsions, microemulsions, solutions, suspensions, and syrups. Osmotically and topically administered compounds may be administered as creams, gels, inhalants, lotions, ointments, pastes, powders, solutions, and sprays. Parenterally administered compounds may be administered as aqueous or oleaginous solutions or aqueous or oleaginous suspensions, the latter of which contains crystalline, amorphous, or otherwise insoluble forms of the compounds. Rectally and vaginally administered compounds may be administered as creams, gels, lotions, ointments, and pastes.

Dosage forms for the compounds depend on the species being treated, the disorder being treated and the severity thereof, the composition comprising the compounds, the time of administration, the route of administration, the duration of treatment, the potency of the compounds, and the rate of excretion of the compounds. The daily therapeutically effective amount of the compounds administered to a patient in single or divided doses range from about 0.1 to about 200 mg/kg body weight, preferably from about 0.25 to about 100 mg/kg body weight. Single dose compositions contain these amounts of the compounds or combinations of submultiples thereof.

Antibacterial activity of the compounds against *Streptococcus pneumoniae* was determined visually by the broth microdilution method described in the National Committee for Clinical Laboratory Standards (1997), "Methods for dilution antimicrobial susceptibility tests for bacteria that grow aerobically," approved standard M7-A4 (Wayne, Pa., USA). All strains tested were from the Abbott Laboratories culture collection and were either clinical isolates or reference strains obtained from the American Type Culture Collection (Manassas, Va., USA).

Twelve petri dishes, each containing successive aqueous dilutions of test compounds in sterilized Brain Heart Infusion agar (Difco 0418-01-5) (10 mL), were inoculated with 1:100 dilutions of the microorganisms in TABLE 1 using a Steers replicator block (or 1:10 dilutions for slow-growing *Streptococcus* strains), co-incubated at 35–37° C. for 20–24 hours with plates containing three commercially-available quinolines one commercially-available oxazolidinone, and a control plate with no compound, and inspected visually to provide the minimum inhibitory concentration (MIC), in μg/mL, by which is meant the lowest concentration of the test compound which yielded no growth, a slight haze, or sparsely isolated colonies on the inoculum spot as compared to growth in the control plate.

TABLE 1

| Microorganism | Code |
| --- | --- |
| Quinoline-Succeptable Streptococcus pneumoniae ATCC 6303 | AA |
| Quinoline-Resistant Streptococcus pneumoniae 7257 | BB |

TABLE 2

| Example | AA MIC | BB MIC |
| --- | --- | --- |
| Ciprofloxacin | 1 | 16 |
| Norfloxacin | 1 | 32 |
| Trovafloxacin | 0.06 | 4 |
| Linezolid | 2 | 0.5 |

The antibacterial activity of the compounds of the invention was superior to the control containing no compound. These data demonstrate that the compounds are antibacterials and are therefore useful for the prophylaxis and treatment of bacterial infections.

Bacterial protein synthesis inhibitory activity of the compounds and the aformentioned commercially-available antibacterials was determined by translation assays performed using the firefly luciferase reporter system described by Murray et al., (2001), "Staphylococcus aureus Cell Extract Transcription-Translation Assay: Firefly Luciferase Reporter System for Evaluating Protein Translation Inhibitors," Antimicrob. Agents Chemother. 45(6): 1900–1904, replacing the Staphylococcus aureus S30 extract described therein with S30 Streptococcus pneumoniae extract from quinoline-succeptable Streptococcus pneumoniae ATCC 46919, and replacing plasmid coding for the luciferase gene with mRNA (encoding produced by in vitro transcription from the plasmid pAS10rbs3) which encoded the luciferase gene with an upstream Streptococcus pneumoniae promoter and Shine-Dalgarno site.

The $IC_{50}$'s of the compounds, defined as concentrations of the same which caused 50% inhibition of bacterial protein synthesis, was greater than about 222 μM.

The $IC_{50}$'s of the quinolines tested were greater than about 100 μM; and the $IC_{50}$ of Linezolid was about 3 μM.

These data demonstrate that the commercially-available quinolones tested do not inhibit bacterial protein synthesis in Streptococcus pneumoniae, even at high concentrations, and that inhibition of bacterial protein synthesis by the compounds is comparable to Linezolid.

Thus, while not being limited to a particular theory, the compounds function by a mechanism more similar to Linezolid (which inhibits bacterial protein synthesis) than quinolines (which inhibit DNA gyrase).

Because the compounds inhibit the growth of quinolone resistant bacteria at least as well as quinolone susceptible bacteria and because they function by a mechanism which differs from quinolines, they are useful not only for prophylaxis and treatment of bacterial infections but also for prophylaxis and treatment of bacterial infections for which quinolines would be ineffective or only partially effective.

The following schemes illustrate representative processes by which the compounds of the invention may be made. It is meant to be understood that the order of the steps in the processes may be varied, other reagents may be substituted for those specifically mentioned, and vulnerable substituents may be protected and deprotected during the process.

Abbreviations used are DME for 1,2-dimethoxyethane; DMF for N,N-dimethylformamide; DMSO for dimethylsulfoxide; and THF for tetrahydrofuran.

SCHEME 1

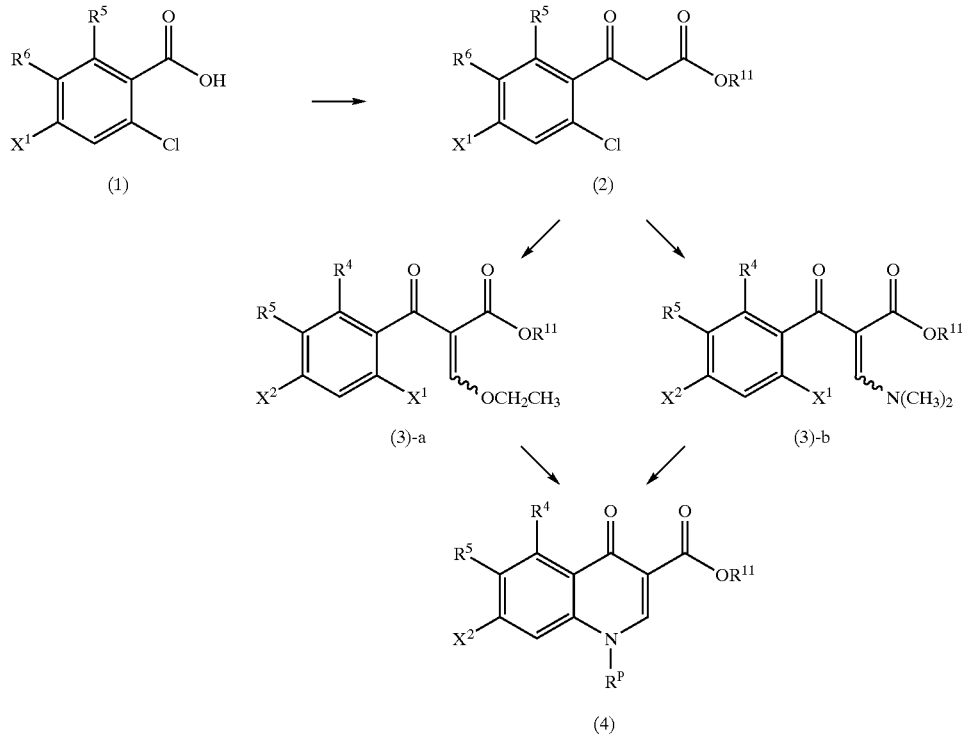

Compounds having formula (1), in which $X^1$ is Br or Cl, may be converted to compounds having formula (2) by (a) reacting the former and a halogenating agent to provide an acid chloride and (b) reacting the product of step (a) and a compound having formula (i)

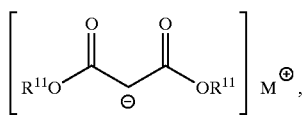

in which M is sodium or potassium.

Halogenating agents include oxalyl chloride/DMF and thionyl chloride. Step (a) is typically conducted at about 25° C. to 50° C., over about 1 to 6 hours, in solvents such as dichloromethane and chloroform. Step (b) is typically conducted at about 0° C. to 25° C., over about 1 to 24 hours, in solvents such as dichloromethane, chloroform, THF, and mixtures thereof.

Compounds having formula (2) may be converted to compounds having formula (3)-a by reacting the former, triethyl orthoformate, and acetic anhydride. The reaction is typically conducted from about 1 to 6 hours, at about 80° C. to 140° C., in acetic anhydride.

Compounds of formula (2) may be converted to compounds of formula (3)-b by reacting the former, 3,3-dimethylaminoacrylate, and triethylamine. The reaction is typically conducted from about 1 to 3 hours, at about 80° C. to 110° C., in solvents such as benzene, toluene, or THF.

Compounds having formulas (3)-a or (3)-b may be converted to compounds having formula (4) by (a) reacting the former and compounds having formula (ii)

$$R^P\text{—}NH_2 \quad (ii),$$

in which $R^P$ is a nitrogen protecting group, and (b) reacting the product of step (a) and a first base. Nitrogen protecting groups include trimethylsilyl, tert-butyl, and triphenylmethyl. First bases include potassium carbonate, sodium carbonate, sodium hydride, and potassium hydride. The reaction is typically conducted from about 24 hours to to 7 days, at about 0° C. to 100° C., in solvents such as dichloromethane, chloroform, acetonitrile, THF, and mixtures thereof.

SCHEME 2

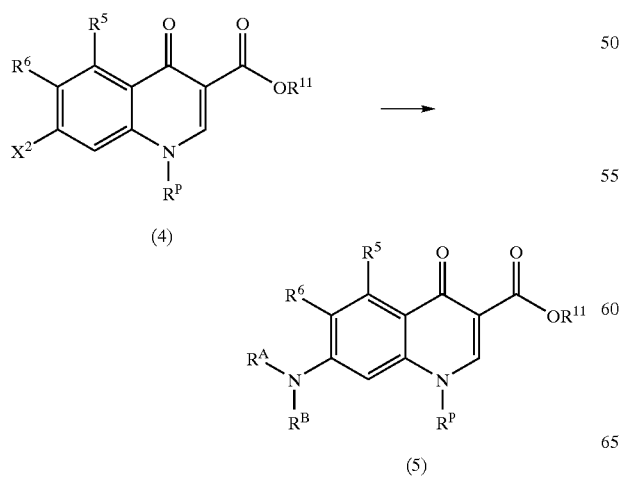

Compounds having formula (4) may be converted to compounds having formula (5) by reacting the former and compounds having formula (iii)

$$NHR^A R^B \quad (iii)$$

in which $R^A$ and $R^B$ combine to form groups embraced by $R^7$ which are attached through a nitrogen atom, and a second base. Second bases include potassium bicarbonate, sodium bicarbonate, potassium phosphate, potassium carbonate, triethylamine, diisopropylethylamine, and 1,8-diazabicyclo-[5.4.0]undec-7-ene. The reaction is typically conducted from about 5 hours to 7 days, at about 25° C. to 160° C., in solvents such as acetonitrile, dichloromethane, chloroform, DMSO, DMF, dimethylacetamide, N-methylpyrrolidine, water, and mixtures thereof.

SCHEME 3

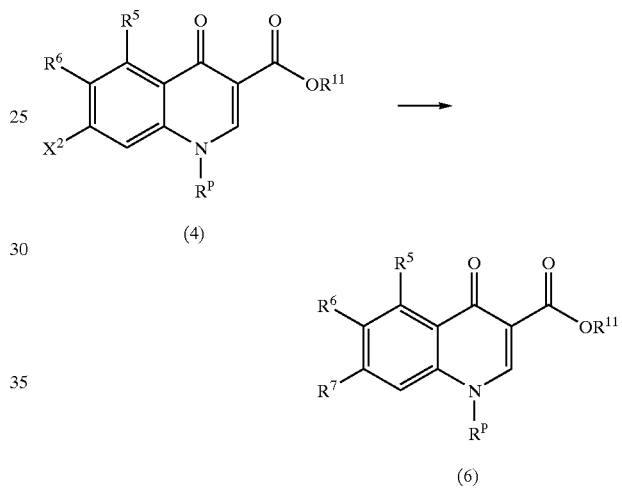

Compounds having formula (4) may be converted to compounds having formula (6), in which $R^7$ is aryl or heteroaryl, by reacting the former and compounds having formula (v), $$R^7\text{-}Q^1 \quad (v),$$

in which $R^7$ is aryl or heteroaryl, $Q^1$ is $B(V^1)_2$ or $Sn(alkyl)_3$, and $V^1$ is alkyl, OH, or $OR^{45}$, in which $R^{45}$ is alkyl, a coupling catalyst, a third base, and, optionally, a first additive. Coupling catalysts include tetrakis(triphenylphosphine)palladium(0), tris(dibenzylideneacetone)dipalladium(0), [1,1'-bis(diphenylphosphino)ferrocene]dichloropalladium (II), and dichlorobis(triphenylphosphine)palladium(II). Fifth bases include potassium bicarbonate, sodium bicarbonate, potassium phosphate, potassium carbonate, cesium carbonate, cesium fluoride, triethylamine, diisopropylethylamine, and 1,8-diazabicyclo-[5.4.0]undec-7-ene. First additives include phosohines such as tributylphosphine, tricyclohexylphosphine, triphenylphosphine, trinaphthylphosphine, tri(fury-2-yl)phosphine, tri(pyrid-3-yl)phosphine, triphenylarsine, 1,4-bis(diphenylphosphino)butane (dppb), 1,2-bis(diphenylphosphino)ethane (dppe), 1,1-bis (diphenylphosphino)methane (dppm), 1,2-bis (dimethylphosphino)ethane (dmpe), and 1,1'-bis (diphenylphosphino)ferrocene (dppf), and salts such as copper(I) iodide and copper(I) chloride. The reaction is typically conducted from about 3 to 24 hours, at about 80° C. to 150° C., in solvents such as benzene, toluene, xylenes, 1,4-dioxane, THF and DMF.

and potassium bis(trimethylslyl)amide. Oxidants include oxygen, hydrogen peroxide, meta-chloroperbenzoic acid, and trimethylborate/sodium bisulfite. The reaction is typically conducted from about 1 to 24 hours, at about −78° C. to 25° C., in solvents such as THF and dioxane.

SCHEME 4

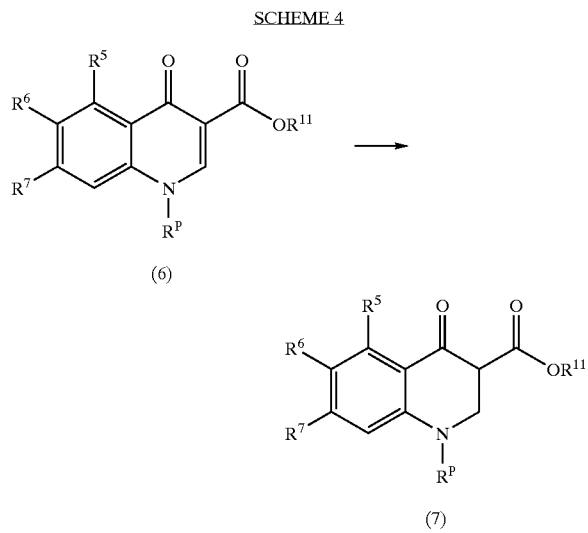

SCHEME 6

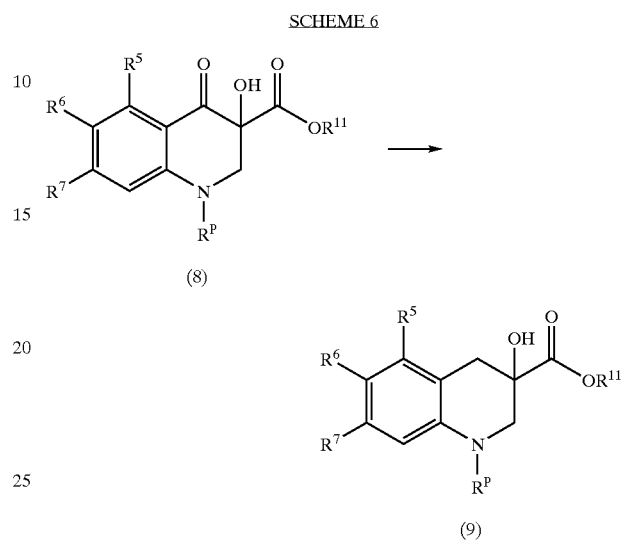

Compounds having formula (6) can be converted to compounds having formula (7) by reacting the former and a hydrogenation catalyst. Hydrogenation catalysts include platinum on carbon with hydrogen gas and triethylsilane with trifluoroacetic acid. The reaction is typically conducted from about 3 to 24 hours, at about 0° C. to 35° C., in solvents such as dichloromethane, chloroform, and carbon tetrachloride.

Compounds having formula (8) can be converted to compounds having formula (9) by reacting the former and a reduction catalyst. Reduction catalysts include sodium borohydride and sodium cyanoborohydride. The reaction is typically conducted from about 1 to 18 hours, at about 0° C. to 35° C., in solvents such as methanol, ethanol, THF, water, and mixtures thereof.

SCHEME 5

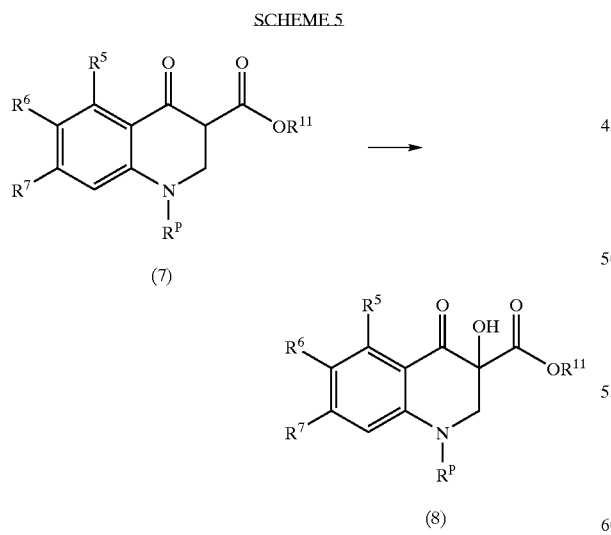

SCHEME 7

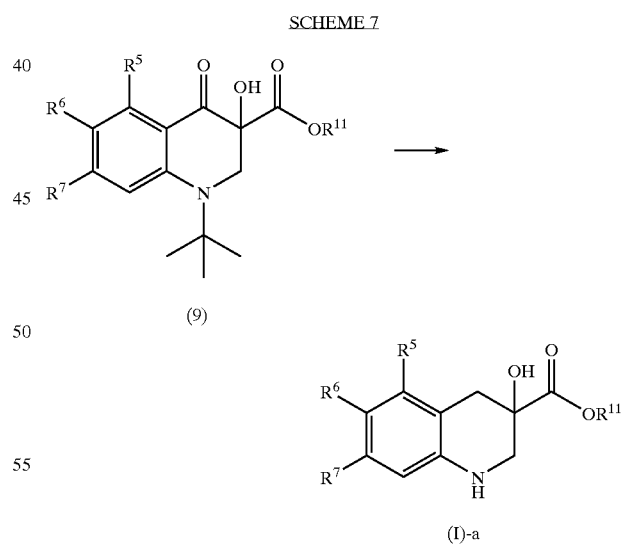

Compounds having formula (7) may be converted to compounds having formula (8) by (a) reacting the former and a fourth base and (b) reacting the product of step (a) and an oxidant. Fourth bases include sec-butyllithium, lithium bis(trimethylslyl)amide, sodium bis(trimethylslyl)amide, Compounds having formula (9) may be converted to compounds having formula (I)-a by reacting the former and an acid. Acids include hydrochloric acid, sulfuric acid, and trifluoroacetic acid. The reaction is typically conducted from about 3 to 24 hours, at about 25° C. to 110° C., and at atmospheric or elevated pressures, in solvents such as THF, 1,4-dioxane, water, and mixtures thereof.

SCHEME 8

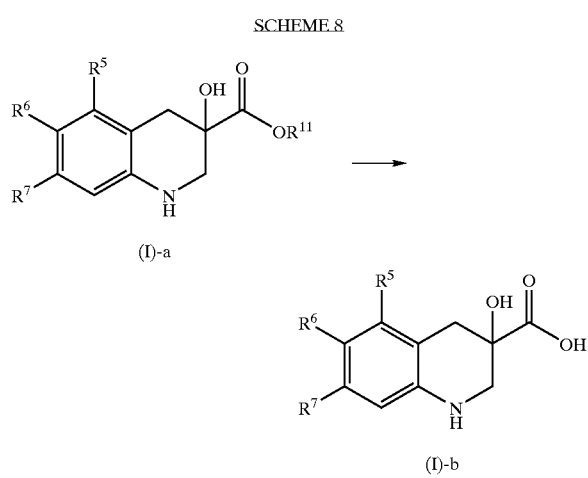

Compounds having formula (I)-a may be converted to compounds having formula (I)-b by reacting the former and a fifth base. Fifth bases include lithium hydroxide, sodium hydroxide, and potassium hydroxide. The reaction is typically conducted from about 3 to 24 hours, at about 25° C. to 110° C. and at atmospheric or elevated pressures, in solvents such as THF, 1,4-dioxane, methanol, ethanol, iso-propanol, dichloromethane, water, and mixtures thereof.

The following examples illustrate methods by which certain preferred embodiments of the invention may be prepared.

EXAMPLE 1

A solution of ethyl 3-(2,6-dichloro-5-fluoro(3-pyridyl))-3-oxopropanoate (40 g) in acetic anhydride (100 mL) was treated with triethylorthoformate (26.1 mL), heated to 85° C. for 6.5 hours, and concentrated; and the concentrate was treated with toluene and concentrated.

EXAMPLE 2

A solution of Example 1 (34.5 g) in acetonitrile (350 mL) was treated with tert-butyl amine (11.3 mL), stirred for 10 minutes, treated with potassium carbonate (28 g), stirred at 80° C. for 3 days and at 85° C. for 16 hours, cooled, and concentrated; and the concentrate was treated with water, filtered, and triturated with ether and hexane.

EXAMPLE 3

A solution of Example 2 (300 mg) in acetonitrile (40 mL) was cooled to 0° C., treated with potassium carbonate (1 g) and 3-(tert-butoxycarbonylamino)pyrrolidine (342 mg), stirred at 60° C. overnight, cooled, treated with ethyl acetate, washed with water, 10% aqueous citric acid, water, and brine, and concentrated; and the concentrate was chromatographed on silica gel with ethyl acetate.

EXAMPLE 4

A solution of Example 3 (2.5 g) in ethanol (100 mL) was treated with sodium borohydride (403 mg), stirred for 2 hours, treated with water, and extracted with ethyl acetate. The extract was washed with water and brine and concentrated under a stream of nitrogen; and the concentrate was and chromatographed on silica gel with ethyl acetate/hexane.

EXAMPLE 5

A solution of Example 4 (785 mg) in THF (30 mL) was cooled to −78° C., treated with 1.3 M sec-butyl lithium in hexane (2.9 mL), stirred for 90 minutes, warmed to 0° C. for 30 minutes, recooled to −78° C., treated with trimethylborate (410 μL), warmed to ambient temperature overnight, cooled to −78° C., treated with 10% aqueous sodium bisulfite, stirred for 90 minutes, and extracted with ethyl acetate. The extract was dried ($Na_2SO_4$), filtered, and concentrated; and the concentrate was chromatographed on silica gel with ethyl acetate/hexane.

EXAMPLE 6

A solution of Example 5 (30 mg), trifluoroacetic acid (35 μL), and triethylsilane (35 μL) in carbon tetrachloride (1 mL) at 0° C. was stirred for 6 hours, treated with trifluoroacetic acid (1 mL) and triethylsilane (1 mL), warmed to room temperature, stirred for 3 days, and concentrated. The concentrate was chromatographed on silica gel with 95:5:5 dichloromethane/methanol/concentrated ammonium hydroxide.

EXAMPLE 7

A solution of Example 6 in 6M HCl (10 mL) at 80° C. was stirred for 6 hours, cooled, and concentrated; and the concentrate was treated with water and lyophilized.

EXAMPLE 8

A solution of EXAMPLE 5 in dioxane (5 mL) was treated with 4M HCl in dioxane (70 μL), stirred for 4 hours at ambient temperature and 2 hours at 40° C., treated with 4M HCl in dioxane (300 μL), heated to 50° C., cooled, and concentrated; and he concentrate was treated with ethyl acetate, washed with concentrated ammonium hydroxide, and concentrated.

Spectral Data for Representative Compounds

EXAMPLE 4

$^1$H NMR 300 MHz (DMSO-$d_6$) δ 7.4 (d, J=13.6, 1H); 7.2 (m, 1H); 4.1 (q, J=7.1, 1H); 4.1 (m, 1H); 3.9–3.5 (m, 6H); 3.4 (m, 1H); 2.1 (m, 1H); 1.9 (m, 1H), 1.5 (s, 9H); 1.4 (s, 9H); 1.2 (t, J=7.1).

EXAMPLE 5

$^1$H NMR 300 MHz (DMSO-$d_6$) δ 7.5 (d, J=13.6, 1H); 7.2 (m, 1H); 6.3 (s, 1H); 4.1 (q, J=7.1, 2H); 4.0 (m, 1H); 3.9 (d, J=12.9, 1H); 3.8–3.5 (m, 4H); 3.3 (m, 1H); 2.1 (m, 1H); 1.9 (m, 1H); 1.5 (s, 9H); 1.4 (s, 9H); 1.2 (t, J=7.1, 3H).

EXAMPLE 7

$^1$H NMR 500 MHz (DMSO-$d_6$) δ 7.1 (d, J=12.7 Hz, 1H), 4.1–3.4 (m, 5H), 3.4 (d, J=12.2 Hz, 1H), 3.2 (d, J=12.2 Hz 1H), 2.9 (d, J=16.1 Hz, 1H), 2.6 (d, J=16.1 Hz, 1H), 2.2 (m, 1), 2.0 (m, 1).

EXAMPLE 8

$^1$H NMR 500 MHz (DMSO-$d_6$) δ 7.4 (d, J=13.7 Hz, 1H); 7.2 (m, 1H), 6.2 (m, 1H), 4.1 (q, J=7.3 Hz, 2H); 3.8–3.7 (m, 2H); 3.7 (dd, J=13.2, 2.9, 1H); 3.6 (m, 1H); 3.5 (m, J=5.4, 1H); 3.3 (m, 2H); 2.0 (ddd, J=12.7, 6.8, 5.9, 1H); 1.6 (ddd, J=12.7, 6.4, 6.4, 1H); 1.1 (t, J=7.3, 3H).

The foregoing is merely illustrative of the invention and is not intended to limit the same to the disclosed compounds. Variations and changes which are obvious to one skilled in the art are intended to be within the scope and nature of the invention which is defined in the appended claims.

What is claimed is:

1. A compound having formula (I)

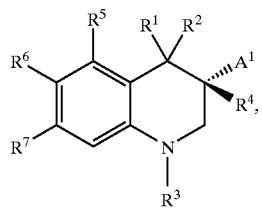

in which
one of $A^1$ or $R^4$ is OH or $OR^{11}$ and the other is C(O)OH or $C(O)OR^{60}$;
$R^1$ and $R^2$ are hydrogen or taken together are =O;
$R^3$ is hydrogen, $C(CH_3)_3$, $O-CH_2CH=CH_2$, or methyl substituted with 2,4-dimethoxyphenyl;
$R^5$ is hydrogen, alkyl, halo, OH, $CF_3$, $CH_2CF_3$, $CF_2CF_3$, or $OR^{11}$;
$R^6$ is hydrogen, halogen, alkyl, CN, $NO_2$, C(O)H, C≡CH, C≡C(alkyl), C≡$CCCl_3$, C≡$CCF_3$, CH=$CH_2$, or $OR^{11}$;
$R^7$ is halo, aryl, heteroaryl, heterocyclyl, bicyclic heterocyclyl, $NH(R^{12})$, or $N(R^{13})(R^{14})$,
in which the aryl is phenyl which is unsubstituted or substituted with one halo substituent,
the heteroaryl is furyl or thienyl,
the heterocyclyl is azetidinyl, piperidinyl, or pyrrolidinyl, each of which is unsubstituted or substituted with a substituent selected from the group consisting of alkyl, $-NH_2$, $-OH$, and $-NH(R^{35})$,
in which $R^{35}$ is alkyl, and
the bicyclic heterocyclyl is six-membered with one or two nitrogen atoms and two non-adjacent carbons attached by a covalent bond or $CH_2$, seven-membered with two nitrogen atoms, eight-membered with 1 nitrogen atom and zero double bonds, eight-membered with two nitrogen atoms, or nine-membered with two nitrogen atoms and zero double bonds, each of which is unsubstituted or substituted with a substituent selected from the group consisting of $-NH_2$, $-NH(R^{35})$, and $-C(O)OR^{35}$,
in which $R^{35}$ is alkyl or alkyl substituted with phenyl.
$R^{11}$ is alkyl, $C(O)R^{70}$, or alkyl substituted with a substituent selected from the group consisting of halo, aryl, $-NH_2$, $-NH(alkyl)$, and $-N(alkyl)_2$;
$R^{12}$, $R^{13}$, and $R^{14}$ are independently alkyl or alkyl substituted with a substituent selected from the group consisting of heterocyclyl, $-NH_2$, $-NH(alkyl)$, and $-N(alkyl)_2$; and
$R^{60}$ and $R^{70}$ are independently alkyl, aryl, or alkyl substituted with a substituent selected from the group consisting of halo, aryl, $-NH_2$, $-NH(alkyl)$, and $-N(alkyl)_2$.

2. A compound of claim 1 having formula (I)

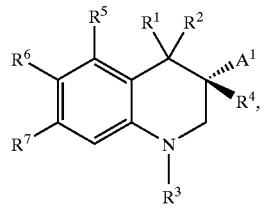

in which
one of $A^1$ or $R^4$ is $-OH$ and the other is $-C(O)OH$ or $-C(O)OR^{35}$;
$R^1$ and $R^2$ are hydrogen or taken together are =O;
$R^3$ is hydrogen or alkyl,
in which the alkyl is $-C(CH_3)_3$;
$R^5$ is hydrogen;
$R^6$ is halo; and
$R^7$ is heterocyclyl,
in which the heterocyclyl is pyrrolidinyl substituted with $-NH_2$.

3. A compound of claim 1 which is ethyl 7-(3-aminopyrrolidin-1-yl)-6-fluoro-3-hydroxy-4-oxo-1,2,3,4-tetrahydro-1,8-naphthyridine-3-carboxylate or 7-(3-aminopyrrolidin-1-yl)-6-fluoro-3-hydroxy-1,2,3,4-tetrahydro-1,8-naphthyridine-3-carboxylic acid.

4. A composition for the treatment of bacterial infections in a fish or a mammal comprising a compound of claim 1 and an excipient.

5. A method for the treatment of bacterial infection in a fish or a mammal comprising administering thereto a therapeutically effective amount of a compound of claim 1.

6. The method of claim 3 in which the bacterial infection is a quinoline-resistant bacterial infection.

* * * * *

UNITED STATES PATENT AND TRADEMARK OFFICE
CERTIFICATE OF CORRECTION

PATENT NO. : 6,818,654 B2
DATED : November 16, 2004
INVENTOR(S) : David Anderson et al.

It is certified that error appears in the above-identified patent and that said Letters Patent is hereby corrected as shown below:

Column 16,
Line 24, replace "-C(O)OR$^{35}$;" with -- -C(O)OR$^{60}$; --.

Signed and Sealed this

Fourteenth Day of February, 2006

JON W. DUDAS
*Director of the United States Patent and Trademark Office*